United States Patent [19]

Nielson et al.

[11] Patent Number: 4,958,460
[45] Date of Patent: Sep. 25, 1990

[54] METHOD OF GROWING AND HARVESTING MICROORGANISMS

[75] Inventors: Jay P. Nielson, Salt Lake City; Paul A. Sturm, Ogden, both of Utah

[73] Assignee: Algae Farms, Salt Lake City, Utah

[21] Appl. No.: 191,993

[22] Filed: May 9, 1988

[51] Int. Cl.$^5$ ............................................. A01G 33/00
[52] U.S. Cl. .................................................. 47/1.400
[58] Field of Search ........................................... 47/1.4

[56] References Cited

U.S. PATENT DOCUMENTS

| | | | |
|---|---|---|---|
| 4,253,271 | 3/1981 | Raymond | 47/1.4 |
| 4,341,038 | 7/1982 | Bloch et al. | 47/1.4 |
| 4,348,285 | 9/1982 | Groeneweg | 47/1.4 |
| 4,554,390 | 11/1985 | Curtain | 47/1.4 |

*Primary Examiner*—James R. Feyrer
*Attorney, Agent, or Firm*—Mallinckrodt & Mallinckrodt

[57] ABSTRACT

A process and system for growing and harvesting algae of the genus Dunaliella, along with their associated bacteria, either in a body of saline water having extensive surface area and shallow depth, or in a tank. In the former the algae are grown in a saline body of water, caused to accumulate in the upper regions of the body of water by the action of light, and caused to aggregate in the upper regions by outflowing the body of water into a first harvesting location by way of a transition channel wherein the body is changed from being shallow and wide to narrow and deep. The upper regions containing the aggregation of algae and associated bacteria are then separated as a slurry and introduced into a second harvesting location wherein salt is introduced into the slurry so as to increase its density thereby causing the algae and associated bacteria to float on the surface. The algae and associated bacteria are then harvested off the surface as a biomass by skimming or other means.

When grown in a tank of saline water the algae and associated bacteria are caused to accumulate in the upper regions by the action of light, the depleted lower regions are discharged from the tank, salt is added to the remaining upper regions thus causing the algae and associated bacteria to float on the surface, and the algae and associated bacteria are then harvested off the surface.

7 Claims, 2 Drawing Sheets

METHOD OF GROWING AND HARVESTING MICROORGANISMS

BACKGROUND OF THE INVENTION

1. Field:

The invention is in the field of production and harvesting of algae, together with their associated bacteria.

2. State of the Art:

Algae are single cell microorganisms, sometimes called algal cells. There are many different types of algae, some of which are commonly known by such layman terms as "pond scums", "frog spittle", "water mosses", "seaweeds", etc. Some algae grow in fresh water and some in brackish water. Some, such as *Dunaliella teodoresco* (usually called just Dunaliella) will even thrive in extremely salty water, e.g. the Dead Sea in Israel, the Huth lagoon in Australia, the Searle's Lake region in California, and the Great Salt Lake in Utah. There are several strains of Dunaliella, e.g. *Dunaliella salina, Dunaliella bardawill*, and others. However, these all have quite similar properties. Algae, even the Dunaliella, are a rich source of food for fish and animals, and are also a source of many other valuable products, such as oil, glycerol, beta-carotene, and others. Consequently, the production and harvesting of algae constitutes an important industry.

In common with practically all living organisms, the various forms of algae also have their predators. Dunaliella has an advantage in that it can thrive in a highly concentrated saline medium wherein few of its predators can survive. Thus, in such a medium, it can grow practically unharmed by predators. In addition the high salt concentration has another advantage in that it considerably increases the production of the valuable b-carotene.

Dunaliella can also exist in saline waters having a low concentration of salt. Thus, in shallow pools or ponds a dilution of the salt content by rainwater or melting snow will not destroy the algae. Because of this ability to thrive in saline waters having a wide range of salt content, it is not necessary to closely control the salt concentration level.

Dunaliella also has a weakness, in that, unlike many other algae, it does not have a strong and rigid outer shell. Thus, it can be easily damaged by mishandling.

Due to its great potential for providing useful products, many schemes have been devised in an attempt to improve the methods of growing and harvesting dunaliella and of extracting the useful products therefrom. This algae and the bacteria associated with it normally grow in a saline liquid medium from which it must be separated. Some prior methods for separating the Dunaliella from the liquid medium have utilized filters. However, the Dunaliella algae are quite small, being ovoids of approximately 25×8–15 micron size, and the bacteria are mostly smaller than five microns. Due to the lack of a rigid cell wall, the cells are quite flexible and can pass through filters as small as five microns. Also, they are quite slimy. The result is that filters, having a small enough mesh size to effectively filter, rapidly become clogged and necessitate a frequent and very difficult cleaning operation. Filter aids, such as diatomaceous earth, have been employed. However, the use of these results in a cake that must be removed and further processed.

Some experimenters have utilized a centrifuge to effect separation. However, since the Dunaliella cells are in a saline solution that usually has a high specific gravity and, since they are substantially neutrally buoyant, centrifuging requires a very high energy input. In addition, centrifuging damages the cells by breaking their outer membranes, resulting in a loss of desirable constituents.

In some cases, both filtration and centrifuging have been augmented by high pressure to increase their effectiveness. However, this results in still greater damage to the tender Dunaliella cells, leading to still further loss of important constituents, such as glycerol and carotenoids.

Chemical separation has also been proposed, but apparently has not been cost effective. However, one such method that has recently been devised comprises floculating the Dunaliella algae with chemical additives. This procedure may prove useful as one step in the harvesting operation of the invention, but by itself would be too costly since large quantities of chemicals would be needed to accomplish floculation in a large volume of water.

More recently, as disclosed by Kessler, U.S. Pat. No. 4,324,067 of Apr. 13, 1982, the use of fibrous material extending down into the liquid medium has been employed to effect the migration of the algal cells to a harvesting zone above the surface of such medium. This, however, entails the use of a large auxiliary structure covering essentially the entire surface area of the growth reservoir. The provision of such a structure is very undesirable from the standpoints of cost, maintenance, light blockage, and the need for protection against the elements.

In summary it should be noted that experience and research has shown that, even under essentially ideal conditions, only about twenty-five grams of Dunaliella algae will grow per cubic meter of growth medium. This is the natural result of conversion of sunlight energy to compounds with stored energy by plants such as algae, and necessitates the utilization of large bodies of water having extensive surface areas to produce large quantities of the algae.

It is evident that there is a real need for an improved process, system, and apparatus for growing and harvesting the algae as a biomass suitable for further processing.

SUMMARY OF THE INVENTION

It has been found by laboratory experiment and observation of natural processes that there are inherent properties of these algae that can be exploited to advantage.

Thus, there is the inherent ability of the algal cells to grow rapidly (multiply) by cell division when placed in a proper medium and supplied with light and appropriate nutrients. This growth rate is particularly effective when the growth medium is highly saline such that it inhibits the natural predators of the algae.

Again, these algae are motile, possess osmoregulatory mechanisms, and are positive phototactic, such that the cells will "swim" toward a light source. They do this by the use of flagella and probably other mechanisms. Thus, if Dunaliella algae are grown in a pond, they will accumulate mostly in the upper part of the water where the sunlight is most intense, even though they are substantially neutrally buoyant. This tendency to rise to near the surface results in airborne carbon dioxide, as well as sunlight, becoming available, both of which are beneficial to the algae. Laboratory experiments have demonstrated that the algae rise at the rate of approximately 0.15 feet per hour.

Also, these algae are substantially neutrally buoyant in a highly saline medium, meaning that they have neither a significant positive nor a significant negative buoyancy. We have found that the algae quite rapidly adjust their buoyancy as the specific gravity of the medium is changed, so that they equilibrate and regain their substantially neutral buoyancy. Such a change in buoyancy can be detected within an hour or so.

While it is desirable to take advantage of all of these properties in an overall process and system they can be separately utilized.

In the overall process and system of this invention, in a first stage the algae are grown in a saline growth medium, supplied with nutrients, and exposed to light to cause them to come together as an aggregate in the upper part of the medium. Then, by effecting a flow of the medium through a transition channel wherein the cross section of the medium is changed from being relatively wide and shallow to being relatively narrow and deep, it becomes economically possible to harvest a slurry concentrate of the algae and associated bacteria by separating the upper part of the medium from the remainder of the medium. Preferably, the medium is also exposed to light during passage of the medium through the transition channel prior to harvesting of the slurry concentrate. This process gently maneuvers and separates the algae without damage to their fragile outer membranes.

A further concentration of the algae and associated bacteria is obtained in a second stage of the process, wherein the algae and associated bacteria in the slurry are caused to float on the surface of the saline medium remaining in the slurry by introducing into the slurry a substance, such as common salt, which increases the density of the medium. This results in the algae having a temporary positive buoyancy which causes them to float on the surface of the medium. The floating algae and associated bacteria are then harvested from the surface of the medium as a comparatively dry biomass.

The growth reservoir may be located outdoors or indoors. When located outdoors, it may be a man-made or naturally occurring lake or pond or channel. It may also be a tank or vat, especially when located indoors. When located outdoors, the light source is normally the sun. When located indoors, artificial light may be employed.

In accordance with the invention, the density-increasing substance may be introduced into the medium as a first step of the process, causing the algae to float on the surface from the upper part of the body of medium to which they had risen because of their phototactic property. If the lower part of the medium is discharged from the reservoir just prior to introduction of the density-increasing substance, the amount of such substance needed is minimized.

In some instances, it may be desirable to employ only the first stage of the process and to evaporate the liquid from the separated upper part of the medium, leaving a substantially dry biomass of the algae and their associated bacteria that contains some residual salt. This is a product which has limited use, such as a feed for certain types of fish or cattle.

It may be desirable after the growth period to recycle a portion of the growth medium, containing the algae and associated bacteria, back to incoming fresh growth medium to serve as seed cells for a new cycle. Likewise, it may be desirable to similarly recycle depleted growth medium, or, alternatively, to subject it to evaporation for precipitating salt therefrom for recovery and commercial use or reuse in the system.

THE DRAWINGS

In the accompanying drawings, which illustrate the best mode presently contemplated for carrying out the invention:

FIG. 1 is a plan view of a complete system depicted in somewhat schematic form;

FIG. 2, a longitudinal sectional view of the first stage harvesting reservoir of the system of FIG. 1, taken along the line 2—2; and FIG. 3, a schematic longitudinal view of the second stage harvesting reservoir of the system of FIG. 1, including surface scraping mechanism.

DETAILED DESCRIPTION OF THE ILLUSTRATED EMBODIMENT

The illustrated overall system is specifically concerned with the production and harvesting of Dunaliella algae and their associated bacteria in a highly saline medium.

The process of the invention is desirably conducted near a large body of saline water 9 that provides a growth medium of the order of 15% to 25% salinity, although this degree of salinity is not critical. There are various bodies of water in the world in which this order of salinity occurs naturally and from which the growth medium can be taken directly and introduced into a growth reservoir. Under other circumstances, the medium must first be treated or concentrated to obtain the desired salinity. This may be accomplished directly in the growth reservoir, or, alternatively, in a treatment reservoir located just ahead of the growth reservoir. Water treatment is accomplished by adding either salt brine or water as required to achieve the desired degree of salinity, or by causing evaporation of at least a portion of the saline water. The necessity or desirability of water pretreatment can vary from location to location of saline water in the world, and even from time to time at a given location.

Once the preferred salinity of the growth medium is established, such medium must be analyzed for determining the presence of needed nutrients. It will usually be found that at least some nutrients are not present in the desired amount for economical growth of the algae and associated bacteria. They must then be added. It will usually be found that carbon, nitrogen, and soluble phosphates must be added in some form or another. There are various ways of doing this, which are known to the art.

In addition to establishing a growth medium with the necessary nutrients, seed cells of the algae and their naturally associated bacteria are required in the growth medium. Though in most natural bodies of saline water seed cells will be present naturally, it will usually be found desirable to augment these with additional cells.

Figure 1:
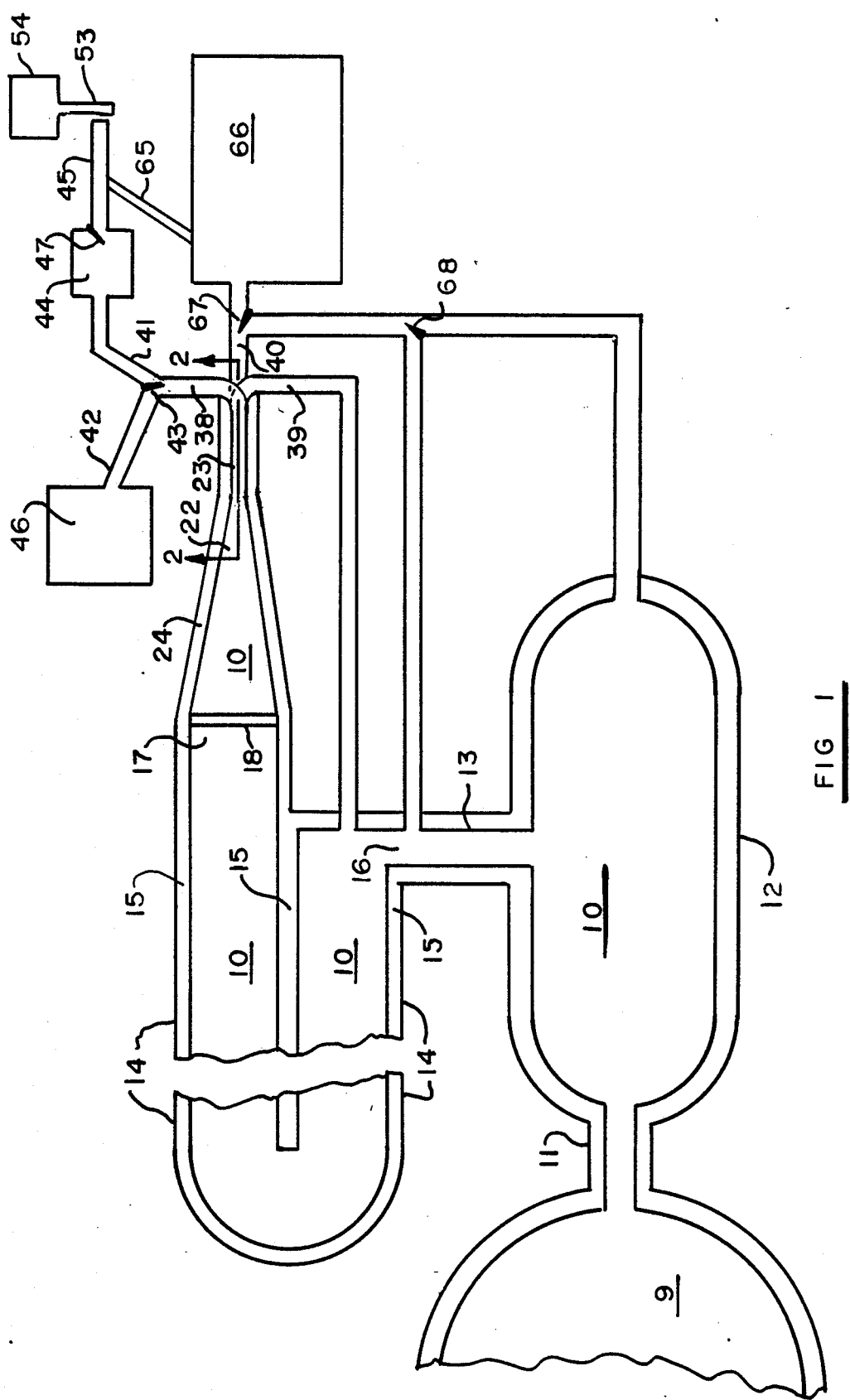

As shown in FIG. 1, the body 9 of saline water, which may be a lake, pond, or even the ocean, supplies a body 10 of liquid growth medium by way of a channel 11 to a treatment reservoir 12 in which a desired degree of salinity is established by the addition of salt or fresh water or by evaporation as needed.

The liquid growth medium 10, adjusted in this manner, is then transported by way of a channel 13 to a growth reservoir 14 that is desirably formed by erecting banks 15 of earth. Nutrients and seed cells of the algae and associated bacteria are introduced into the growth reservoir.

Figure 2:
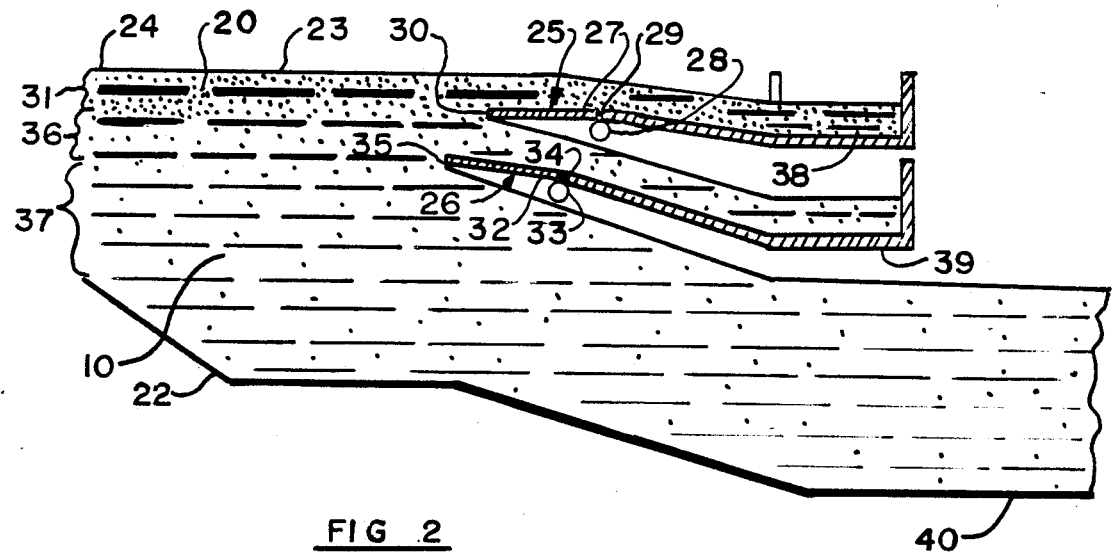

Reservoir 14 is preferably configured as a long canal that is wide but shallow as compared to usual storage reservoirs. Typically, such canal is in the shape of a "U" 1000 or so feet wide, two or so feet deep, and a few miles long. Thus, the cross sectional width to depth ratio is at least about 500 to 1. While such an arrangement is advantageous where area and terrain are favorable, other configurations or considerably smaller tanks or vats may be employed. When a canal such as 14 is employed, it is preferably pitched such that the time for any unit volume of the growth medium to flow from the inlet 16 to the outlet 17 is approximately equal to the desired growth period for the algae, which may be ten to fifteen days. A gate 18 may be provided to control the rate of flow if found necessary or desirable. During the growth period, a light source such as the sun is allowed to shine on the surface of the body of growth medium 10. This results in migration of the algal cells and associated bacteria into the upper part of such medium, as indicated in FIG. 2, forming a biomass 20.

Commencing at the outlet 17 FIG. 1, of the growth reservoir 14, and continuing to the inlet 22 of a first stage harvesting reservoir 23 constituting a harvesting area, there is preferably a transition channel 24 through which the medium 10 flows. This channel changes in cross section from being relatively wide and shallow at 17 to relatively narrow and deep at 22, as shown in FIGS. 1 and 2, its width being convergent and its depth increasing along its length for this purpose. Typically, the cross section will change from being 1000 feet wide and two feet deep to being ten feet wide and ten to forty feet deep. Thus, the cross sectional width to depth ratio is about within the ranges of 1 to 1 and 1 to 4. Preferably, the surface of the medium will be exposed to light while in the transition channel.

This transition of cross section along the length of transition channel 24 results in a concentration of the algae and associated bacteria in the upper few feet of the now very narrow and deep body of medium, especially when augmented by light shining on the surface of the medium. Most of the algae will be in the upper few feet of the medium by the time the medium reaches the inlet 22 of the first stage harvesting reservoir. Typically, the length of transition channel 24 will be approximately 1000 feet, or more.

The first stage harvesting reservoir 23 may also configured as a channel, typically ten feet wide and sloping to from forty to fifty feet deep. Emplaced in this first stage harvesting reservoir is a first skimmer 25 and a second skimmer see FIG. 2 26.

Skimmer 25 is in the form of a flat plate 27, which is approximately as wide as the reservoir and is substantially horizontally disposed. Plate 27 is pivoted about an axis 28 at its downstream edge 29, and its leading edge 30 is adapted to be raised and lowered by suitable mechanism (not shown) under the control of an operator. The downstream edge is preferably located approximately two feet deep, and the leading edge is adjustable, preferably from approximately two inches deep to approximately two feet deep. Thus, this skimmer can skim off the uppermost part 31, i.e. band of the medium 10 within a vertical range of approximately two inches to approximately two feet.

Second skimmer 26 is also in the form of a flat plate 32, which is approximately as wide as the harvesting reservoir and substantially horizontally disposed beneath plate 27. Plate 32 is pivoted about an axis 33 at its downstream edge 34, and its leading edge 35 is adapted to be raised and lowered. The downstream edge 34 is located approximately four feet deep, and the leading edge 35 is adjustable from approximately three inches deep to approximately four feet deep. Thus, this skimmer can skim off the intermediate part 36 of the medium 10, adjustable from approximately three inches to approximately four feet. Plate 32 will always be adjusted such that its leading edge 35 is lower than the leading edge 30 of plate 27.

With this configuration, then, the uppermost part 31 contains the bulk of the aggregation of algae and associated bacteria, the intermediate part 36 contains a lesser amount, and the lowermost part 37 is substantially depleted. The uppermost part 31 is conveyed away from the first stage harvesting reservoir by a conduit 38, the intermediate part by a conduit 39, and the lowermost part by a conduit 40, all as shown in FIGS. 1 and 2. Typically, these conduits are troughs or channels FIG. 2. Conduit 38 branches into two branch conduits 41 and 42. A gate 43 controls the amount that flows into such branch conduits.

Branch conduit 41 conveys a portion of the uppermost part of the medium 31 to a buffer reservoir 44 located intermediate the first stage harvesting reservoir 23 and a second stage harvesting reservoir 45. Branch conduit 42 conveys a portion of the uppermost part of the medium 31 to an evaporation reservoir 46. Typically, the greater portion of uppermost part 31 will flow through branch 41 to buffer reservoir 44 and a lesser portion to evaporation reservoir 46. The medium in evaporation reservoir 46 is caused or allowed to evaporate, thus resulting in an approximately dry biomass of algae and associated bacteria that contains some residual salt. This product is suitable for some uses, such as feed for certain types of animals and fish. However, the salt renders it unusable for some other applications.

Evaporation reservoir 46 may actually be a plurality of reservoirs into which the uppermost part 31 flows successively such that evaporation can be taking place in one or more reservoirs while filling is taking place in another reservoir.

Reservoir 44 serves as a buffer between the operations in the first stage harvesting reservoir 23, which are substantially continuous, and the operations in the second stage harvesting reservoir 45, which are cyclic. Thus, at the start of a cycle, gate 47 is opened to allow the uppermost part 31 in buffer reservoir 44 to be discharged rapidly into second stage harvesting reservoir 45, which is substantially empty at the start of the cycle. Gate 47 is then closed. The uppermost part 31 continues to flow slowly into buffer reservoir 44, which is such that buffer reservoir 44 does not refill until a new cycle is ready to commence.

Figure 3:
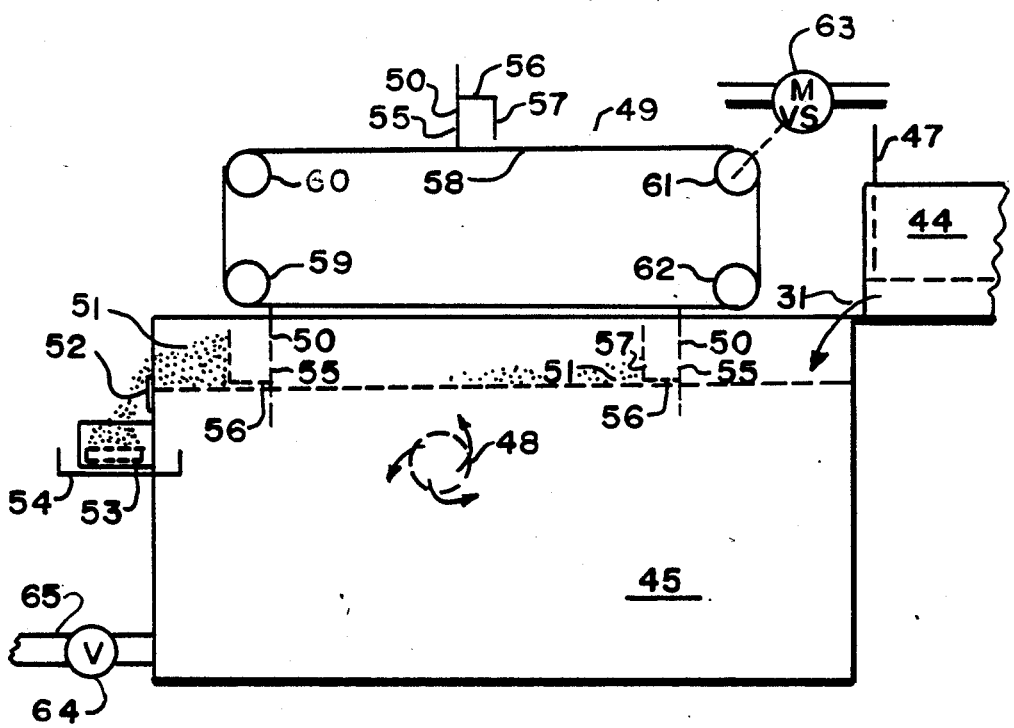

After the medium has filled the uppermost part 31 of the second stage harvesting reservoir 45 and the gate 47 has been closed, salt is dispersed into such medium by means of one or more spargers 48, as shown in FIG. 3. This, then, increases the density of the medium. The algae, being substantially neutrally buoyant before the density increase, now become positive buoyant in the more dense medium, and thus rise to the surface and float on the surface. In time, if left alone, they will readjust their buoyancy to neutral in the more dense medium and thus start to sink below the surface. However, this will not commence for an hour or so. During this hour, the algae and associated bacteria are harvested from the surface of the medium. This is effected as by means of the harvester 49 shown in FIG. 3.

Harvester 49 incorporates a plurality of skimmers 50, which skim the algae 51 from the surface of the medium pushing them over a weir 52 onto a conveyor 53 from whence they are conveyed to a processing location 54 as shown in FIGS. 1 and 3.

Each skimmer 50 comprises a vertically disposed member 55, which extends part way down into the medium; a horizontally disposed member 56 attached to member 55 at a point just above the surface of the medium; and another vertically disposed member 57 attached to the leading edge of member 56, all as shown in FIG. 3. Each skimmer 50 is attached to an endless chain 58, which, in turn, is wrapped around pulleys 59, 60, 61, and 62. Preferably an adjustable speed motor 63 drives one of the pulleys, which causes endless chain 58 to cycle continuously.

In operation, one of the skimmers 50 is inserted into the medium at one extremity of the reservoir and is pulled across the surface of the reservoir, pushing the algae ahead of it until the skimmer reaches the opposite extremity of the reservoir, at which point the algae and associated bacteria are pushed over the weir 52. The skimmer is then raised out of and above the surface of the medium and cycled back to its starting position.

After the algae and their associated bacteria are substantially all removed from the surface of the medium, a valve 64 at the bottom of the second stage harvesting reservoir 45 is opened and the depleted medium is discharge through a conduit 65. After the reservoir has been emptied, valve 64 is closed, gate 47 is opened, and a new cycle starts. The construction is preferably such that the cycle is completed in approximately one hour or less.

The algae and associated bacteria collected in processing location 54 are allowed to dry. They will be in the form of a biomass of algal cells and accompanying bacteria, with very little residual salt.

The depleted medium in conduit 65 may be conveyed to a salt precipitation reservoir 66, where it is allowed to partially evaporate resulting in a precipitation of the included salts, which may then be harvested in known manner. Salt precipitation reservoir 66, in fact, may be a plurality of individual reservoirs. Alternatively, the depleted medium may be cycled back to growth reservoir 14 or to treatment reservoir 12 so as to serve as new growth medium.

Referring now to FIGS. 1 and 2, it can be seen that the intermediate part 36 of the medium flowing from first stage harvesting reservoir 23 in conduit 39 is recycled back to growth reservoir 14, so as to effect an introduction of seed cells into the growth medium.

In addition, the lowermost part 37 of the medium flowing from first stage harvesting reservoir 23 in conduit 40 is recycled back into treatment reservoir 12, so as to serve as new growth medium. Alternatively, such medium may be recycled back directly to growth reservoir 14 or to salt precipitation reservoir 66 for recovery of the included salts. The particular route of the medium will vary from geographical location to geographical location of the system and also from time to time at a given location, being dependent largely on the natural salinity of the body of saline water 9. The actual route may be controlled by gates 67 and 68.

Throughout the system, it may be necessary to provide pumps to aid in conveyance of the medium. The need for and location of such pumps will depend on the geographical location of the system. To the extent possible, gravity will be utilized to cause flow of the medium, assisted by pumps only as needed.

In some instances, it may be desirable to carry out the entire operation in a single reservoir, such as a tank or a vat. The growth medium is introduced into the reservoir; seed cells of the algae and nutrients for the algal cells and associated bacteria are introduced; and light is allowed or caused to shine on the surface of the medium during the growth period, thus inducing the algae to migrate to the upper part of the medium. Following the growth period, salt is dispersed into the medium, thus causing the algae to float on the surface; then the algae are harvested from the surface. It will usually be advantageous to discharge the lower part of the medium from the reservoir just prior to introduction of the salt so as to reduce the amount of salt needed.

As previously indicated, only the first stage may be employed, the separated uppermost part of the medium being allowed or caused to evaporate, thus leaving a substantially dry biomass of algae and associated bacteria which is a suitable end product for certain uses.

It should also be realized that only the second stage may be employed, the algae being allowed to grow throughout the medium and, after a suitable growth period, salt being introduced into the medium, thereby causing the algae to float on the surface, from where they are harvested.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. A process for the reproduction and harvesting of algae of the genus Dunaliella and associated bacteria, comprising the steps of:
   providing a culture zone of a saline liquid growth medium having a cross-sectional width to depth ratio of at least about 500 to 1 and a length allowing sufficient production of algae for harvest;
   providing a harvest zone having a cross-sectional width to depth ratio of about within the ranges of 1 to 1 and 1 to 4;
   providing a graduated transition zone fluidly communicating said culture zone and said harvest zone;
   exposing said production, transition, and harvest zones to light to allow said algae to agglomerate and remain near the surface of said medium;
   flowing the medium through said culture, transition, and harvest zones, whereby said agglomerated algae is concentrated into a horizontal band having vertical depth at the surface of the medium; and,
   separating said band from the remainder of said medium to effect harvest of said algae.

2. A process in accordance with claim 1, wherein the harvested algal is subjected to evaporation to substantial dryness.

3. A process in accordance with claim 2, wherein the salinity of the medium is sufficiently concentrated to be hostile to at least one of the natural predators of the algae.

4. A process in accordance with claim 1, wherein seed cells of the algae are introduced into the body of growth medium to augment any that may be present naturally therein.

5. A process in accordance with claim 1, wherein nutrients are introduced into the medium to augment any that may be present naturally therein.

6. A process according to claim 1, comprising the additional steps of adding a soluble material to the band separated from the remainder of the medium for increasing the density of said band and for thereby causing algae and associated bacteria to float on the surface of said band; and harvesting the floating algae and associated bacteria from said surface of said band.

7. A process in accordance with claim 6 wherein the soluble substance that is introduced into the band separated from the remainder of the medium to increase its density is a salt that increases the salinity of the medium.

* * * * *

UNITED STATES PATENT AND TRADEMARK OFFICE
CERTIFICATE OF CORRECTION

PATENT NO. : 4,958,460

DATED : September 25, 1990

INVENTOR(S) : Jay P. Nielson

It is certified that error appears in the above-identified patent and that said Letters Patent is hereby corrected as shown below:

Column 7, line 33-34, "discharge" should be "discharged"
Column 8, line 65, "algal" should be "algae"

Signed and Sealed this

Third Day of March, 1992

Attest:

HARRY F. MANBECK, JR.

*Attesting Officer*      *Commissioner of Patents and Trademarks*